(12) United States Patent
Thibaudeau et al.

(10) Patent No.: US 6,440,417 B1
(45) Date of Patent: Aug. 27, 2002

(54) ANTIBODIES TO ARGATROBAN DERIVATIVES AND THEIR USE IN THERAPEUTIC AND DIAGNOSTIC TREATMENTS

(75) Inventors: Karen Thibaudeau, Montreal (CA); Dominique Blanchard, Nantes (FR); Dominique P. Bridon, Outremont (CA); Alan M. Ezrin, Moraga, CA (US); Margaret Hardy; Nissab Boudjellab, both of Montreal (CA)

(73) Assignee: ConjuChem, Inc., Montreal (CA)

( * ) Notice: Subject to any disclaimer, the term of this patent is extended or adjusted under 35 U.S.C. 154(b) by 0 days.

(21) Appl. No.: 09/434,605

(22) Filed: Nov. 5, 1999

Related U.S. Application Data
(60) Provisional application No. 60/107,475, filed on Nov. 6, 1998.

(51) Int. Cl.$^7$ .................. C07K 16/44; A61K 39/395; A61K 39/44; A61P 7/02; C07H 19/00
(52) U.S. Cl. .................. 424/134.1; 424/9.1; 424/142.1; 424/143.1; 424/145.1; 424/94.5; 424/530; 435/388.2; 514/311; 536/23.5; 546/153; 546/166; 546/172; 530/391.1
(58) Field of Search .................. 536/23.5; 514/311, 514/314; 530/391.1; 546/153, 166, 172; 424/134.1, 142.1, 143.1, 145.1, 94.5, 530; 435/388.2

(56) References Cited

U.S. PATENT DOCUMENTS 5,612,034 A     3/1997   Pouletty et al.
5,840,733 A   * 11/1998   Krantz .................. 514/311

OTHER PUBLICATIONS

Cruse et al. Illustrated Dictionary of Immunology, Edited by Cruse et al. 1995, pp. 178.*
Coding et al. Monoclonal Antibodies Principles and Practice 1996, Third edition. Haicourt Race and Company Publishers, pp. 62–62, pp. 141–180, and pp. 465–475.*
Separation of 21–(r)– and 21_S) – Argatroban: Solubility and Activity of the Individual Diastereoisomers, Journal of Pharm. Sciences, vol. 82, No. 6, (1993).

* cited by examiner

*Primary Examiner*—Ali R. Salimi
*Assistant Examiner*—Bao Qun Li
(74) *Attorney, Agent, or Firm*—Morrison & Foerster LLP

(57) ABSTRACT

Antibodies to a therapeutic agent and its derivatives and conjugates are disclosed, including antibodies to argatroban and its derivatives and conjugates. The antibodies are useful as reagents in assays and diagnostic kits for determining the concentration of a therapeutic agent or its derivatives and conjugates in biological samples, and further have therapeutic uses in treatment for potential toxicity associated with stable therapeutic conjugates and derivatives, both in vivo and ex vivo.

10 Claims, 3 Drawing Sheets

ANTIBODIES TO ARGATROBAN DERIVATIVES AND THEIR USE IN THERAPEUTIC AND DIAGNOSTIC TREATMENTS

RELATED APPLICATION

This application claims the benefit under 35 U.S.C. § 119(e) of U.S. application Ser. No. 60/107,475, filed Nov. 6, 1998, and is hereby incorporated by reference in its entirety.

FIELD OF THE INVENTION

This invention relates to antibodies to argatroban and argatroban derivatives and their use in medicine. In particular, this invention relates to the field of detection of argatroban and argatroban derivatives and the inactivation, removal and/or sequestration of argatroban and argatroban derivatives using antibodies specific for argatroban and argatroban derivatives.

BACKGROUND OF THE INVENTION

Maintenance of therapeutic agents at effective therapeutic levels is of critical importance in providing effective treatment for a host of conditions. In many treatment methods, effective therapeutic levels are only achieved by repetitive administrations of agents due to short half-lives of the particular agents in vivo. Often, large boluses of agent are administered, leading to initial concentrations above therapeutic levels, which may have adverse effects, followed by sub-optimal concentrations as the agent is degraded or cleared. U.S. Pat. No. 5,612,034 addresses this limitation by providing a method for prolonging the lifetime of an agent in the bloodstream by covalently linking derivatized agents to serum proteins and blood cells. The use of these derivatives presents new needs for analytical reagents to monitor the course of treatment. In addition, the use of these derivatives presents a need for means to inactivate, remove or sequester the derivatives and resulting conjugates during courses of treatment where toxicity or other adverse effects associated with the derivatives or resulting conjugates may be of concern.

As an example, the administration of the synthetic thrombin inhibitor argatroban: 1-[5-(Aminoiminomethyl)amino]-1-oxo-2-[[(1,2,3,4-tetrahydro-3-methyl-8-quinolinyl) sulfonyl]-amino]pentyl]-4-methyl-2-piperidinecarboxylic acid, is a preferred treatment of thrombosis. The efficacy of argatroban, as well as other thrombin inhibitors such as heparin, is limited by its short half-life in patients. In order to address this limitation, active derivatives of argatroban were synthesized whose half-life in the bloodstream is extended considerably compared to the parent molecule, as described in U.S. Pat. No. 5,840,733, incorporated herein by reference. The increase in persistence is due to the covalent linkage of reactive moieties of the argatroban derivatives to cells or stable serum proteins upon administration. These argatroban derivatives are favored because they enable administration of a more constant therapeutic level of anti-thrombin activity as compared to the available treatments, which require frequent administrations of large boluses of drug, followed by cycles of sub-optimal concentrations in the patient.

While these argatroban derivatives provide benefits in the treatment of thrombosis, their use presents new needs for analytical reagents to monitor the course of treatment. In particular, it is necessary to monitor the level of the derivatized argatroban molecule in vivo in order to adjust the dosage schedule to ensure maintenance of proper levels within the patient. Furthermore, the desirable increased stability of these argatroban derivatives in vivo might lead to new problems during treatment. Because argatroban-blood component conjugates are not rapidly cleared from the bloodstream, the possibility for toxicity is increased. Unlike heparin, whose toxic doses may be treated by protamine sulphate, there are no known antagonists to argatroban. Thus, there is also a need to identify a means to efficiently inactivate, remove or sequester argatroban conjugates from the blood stream in vivo in order to treat patients who suffer unacceptable amounts of bleeding or other side-effects associated with thrombolytic treatment.

SUMMARY OF THE INVENTION

The present invention is directed to isolated and purified antibodies that specifically bind argatroban and argatroban derivatives. The antibodies of this invention specifically bind argatroban derivatives including such derivatives as argatroban-C6-NHS, argatroban C-12-NHS, argatroban C-13 maleimide, argatroban C21-PE maleimide and argatroban C-18 maleimide.

The present invention is further directed to a kit for detecting the concentration of argatroban or argatroban derivatives in a solution such as a blood or serum sample comprising an antibody that specifically binds argatroban and argatroban derivatives. The antibody in the kit may be conjugated to an indicator reagent. The kit may further comprise reagents for performing immunoassays including ELISA, RIA, Western Blot, immunohistochemistry and flow cytometry reagents.

The present invention further relates to methods for determining the A concentration of an argatroban derivative and conjugates of argatroban in biological samples, in particular to methods that employ antibodies specific for the agent or its derivatives and conjugates. In addition, the invention relates to the use of these antibodies as a treatment for potential toxicity associated with stable argatroban conjugates. In one aspect of the invention, the invention relates to methods for determining the concentration of argatroban or its derivatives and conjugates in biological samples using antibodies specific to argatroban or its derivatives and conjugates, and to the use of such antibodies as a treatment for toxicity potentially associated with stable argatroban conjugates.

A third aspect of this invention relates to the use of monoclonal antibodies for the detection, separation and purification of diastereoisomeric mixtures of argatroban and argatroban derivatives.

BRIEF DESCRIPTION OF THE DRAWINGS

This invention will be better understood by reference to the drawings, in which.

DETAILED DESCRIPTION OF THE INVENTION DEFINITIONS

Figure 1:
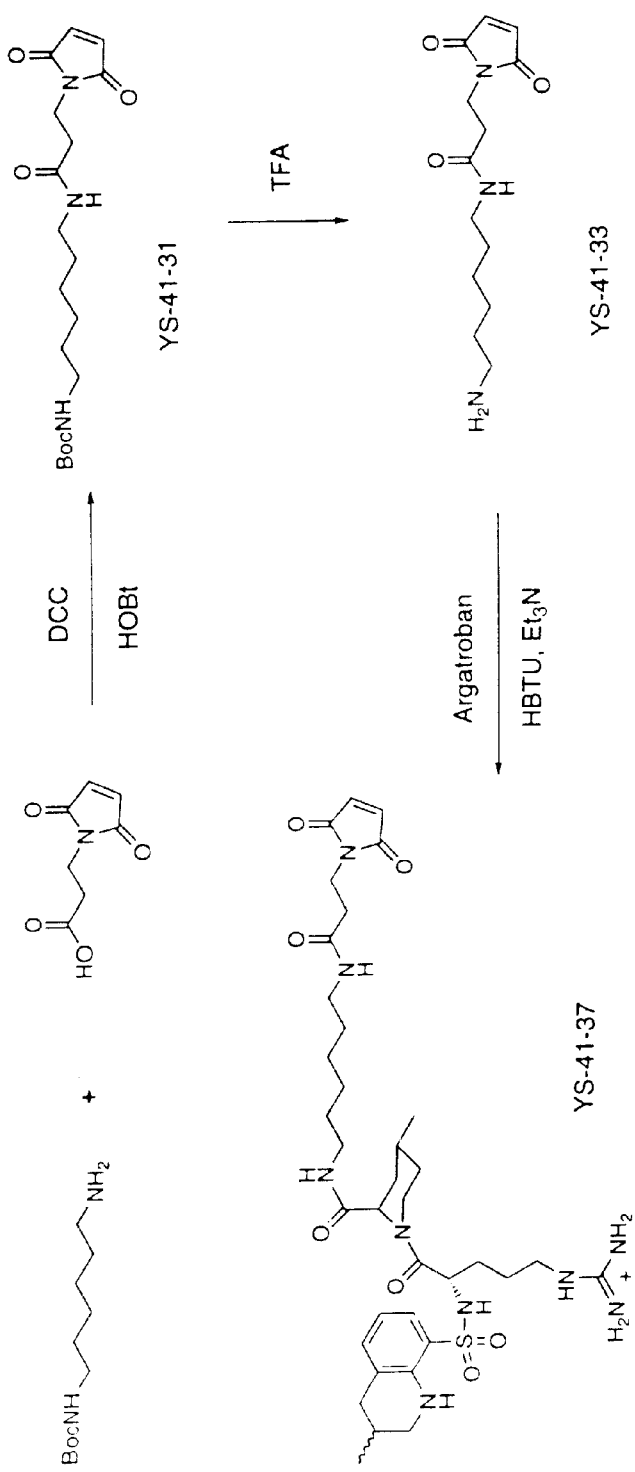
FIG. 1 is a schematic showing the synthesis of argatroban C13 maleimide.

To ensure a complete understanding of the invention the following definitions are provided.

Argatroban derivatives: Argatroban derivatives are modifications of the synthetic thrombin inhibitor argatroban 1-[5-(Aminoiminomethyl)amino]-1-oxo-2-[[(1,2,3,4-tetrahydro-3-methyl-8-quinolinyl)sulfonyl]-amino]pentyl]-4-methyl-2-piperidinecarboxylic acid, where linkers and chemically reactive groups have been coupled to argatroban in such a way to preserve the thrombolytic activity of the derivative. These reactive groups are capable of forming a covalent bond and are generally stable in an aqueous environment, such as blood. Functionalities that are available on proteins for covalent bonding to the reactive groups are primarily amino groups, carboxyl groups, and thiol groups. To form amide bonds, the reactive groups will usually be a carboxy, or carboxy ester, where the ester group is of 1–8, more usually 1–6 carbon atoms, particularly a physiologically acceptable leaving group which activates the carboxy carbonyl for reaction with amino groups in an aqueous system, e.g. N-hydroxysuccinimide (NHS), N-hydroxysulfosuccinimide (sulfo-NHS), maleimide-benzoyl-succinimide (MBS), gamma-maleimido-butyryloxy succinimide ester (GMBS) and maleimidopropionic acid (MPA), isocyanate, thiolester, thionocarboxylic acid ester, imino ester, mixed anhydride, e.g. carbodiimide anhydride, carbonate ester, phosphoryl ester, etc. and the like. In other cases, reactive groups such as azido, diazo, carbodiimide anydride, hydrazine, dialdehydes, thiol groups, or amines can be used to form amides, esters, imines, thioethers, disulfides, substituted amines, or the like. Argatroban derivatives are also known as thrombin inhibitor or TI derivatives.

Anti-argatroban antibodies: Antibodies, either monoclonal or polyclonal, having specificity for argatroban or argatroban derivatives and generated or derived from a host immunized with argatroban or argatroban derivatives or other immunogen based on argatroban. Preferred antibodies will have high specificity and affinity for native, derivatized and conjugated forms of argatroban. The antibodies can also be labelled with enzymes, radiolabels, fluorochromes, fluorophores, chromophores, chemiluminophores, chelates and others.

Diagnostic tests: Diagnostic tests are utilized in any method employing anti-therapeutic agent antibodies to qualitatively or quantitatively determine the presence or concentration of native, derivatized and conjugated forms of the therapeutic agent. For example, radioimmunoassay (RIA) or enzyme-linked immunoassay (ELISA) can be performed on whole blood samples taken from a patient being treated with a therapeutic agent derivative. As another example, immunohistochemical analysis and tissue labelling of tissue and cell samples can be performed. Diagnostic tests may also be packaged as kits that include anti-therapeutic agent antibodies, carriers, reagents, buffers and controls.

Therapeutic uses of anti-argatroban antibodies: Anticipated therapeutic uses of anti-argatroban antibodies would include treatment for toxicity induced by the administration of the argatroban derivatives. Ex vivo methods will include immunodialysis treatment for toxicity employing anti-argatroban antibodies fixed to solid supports. In vivo methods will include administration of anti-argatroban antibodies in amounts effective to induce clearance of antibody-agent complexes.

DETAILED DESCRIPTION

Taking into account these definitions, the invention is directed to antibodies to argatroban and its derivatives and conjugates, and the use of these antibodies for diagnostic and therapeutic purposes, both in vivo and ex vivo.

In its first aspect, the invention is directed to antibodies specific for argatroban or its derivatives and conjugates and to methods that utilize the antibodies to determine the concentration of argatroban or its derivatives and conjugates in biological samples. The invention contemplates the use of such antibodies, and modifications thereof, as reagents in the development and manufacture of immunoassays and diagnostic test kits, including ELISA based assays or kits.

In its second aspect, the invention is directed to the use of these antibodies in methods of treatment for potential toxicity associated with argatroban conjugates. The antibodies can be used to inactivate and remove argatroban derivatives and conjugates from a patient's bloodstream. For example, antibodies can be administered in vivo to a patient for passive immunization. Fixed or otherwise immobilized antibodies can be used for ex vivo immunoadsorbtion of argatroban derivatives and conjugates from a patient's blood.

In a third aspect of the invention, the antibodies are specific for argatroban and its derivatives and conjugates. The argatroban derivatives will, for the most part, have the following formula:

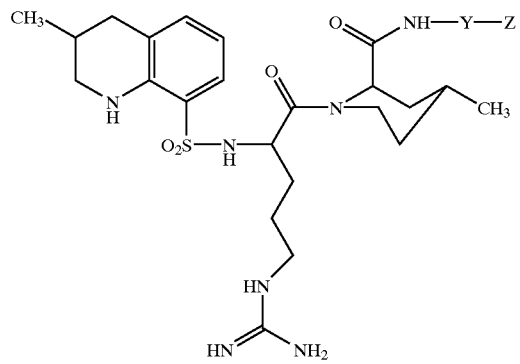

wherein:

Y is a linking group having from 2–100, more usually from 2–18, preferably from 6–12 atoms in the chain, particularly carbon, oxygen, phosphorous and nitrogen, more particularly carbon and oxygen, where Y may be alkylene, oxyalkylene, or polyoxyalkylene, preferably an alkyl chain having from 2–15, more preferably from 6–12 carbon atoms in the alkyl chain, and the like; and Z is a chemically reactive group or precursor to a chemically reactive group, such as carboxy, carboxy ester, where the ester group is of 1–8, more usually 1–6 carbon atoms, particularly a physiologically acceptable leaving group which activates the carboxy carbonyl for reaction with amino groups in an aqueous system, e.g. N-hydroxysuccinimide, N-hydroxysulfosuccinimide, maleimide-benzoyl-succinimide (MBS), gamma-maleimido-butyryloxy succinimide ester (GMBS) and maleimidopropionic acid (MPA), isocyanate, thiolester, thionocarboxylic acid ester, imino ester, mixed anhydride, e.g. carboduimide anhydride, carbonate ester, phosphoryl ester, etc. and the like.

Preferred argatroban derivatives include the following molecules where Y-Z of the above argatroban derivative is specifically defined as follows.

Scheme I presents Argatroban Cl 3-Maleimide.

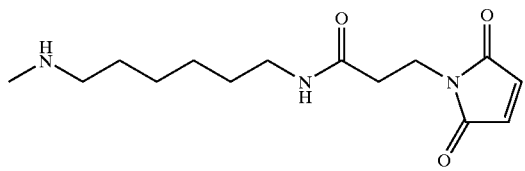

Scheme II presents Argatroban Cl18-Maleimide.

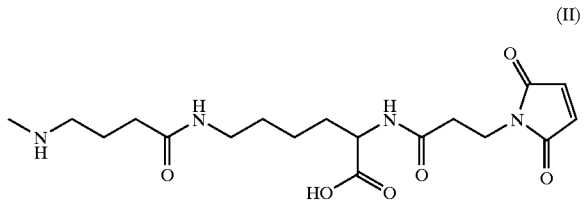

Scheme III presents Argatroban C21-Maleimide.

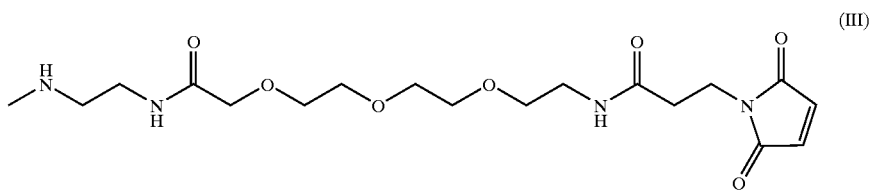

Scheme IV presents Argatroban C12SMCC-Maleimide.

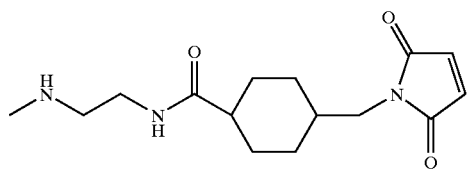

Scheme V presents Argatroban C16SMCC-Maleimide.

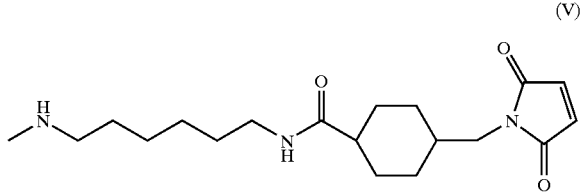

Scheme VI presents Argatroban C8 PE NHS

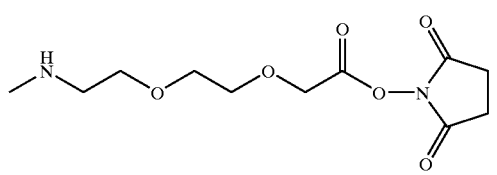

The functionalities which are available on proteins for covalently bonding to the chemically reactive group of argatroban derivatives are primarily amino groups, carboxyl groups and thiol groups. While any of these may be used as the target of the chemically reactive group on the thrombin inhibitor, for the most part, bonds to amino groups will be employed, particularly with the formation of amide bonds. To form amide bonds, one may use as a chemically reactive group a wide-variety of active carboxyl groups, particularly esters, where the hydroxyl moiety is physiologically acceptable at the levels required. While a number of different hydroxyl groups may be employed, the most convenient would be N-hydroxysuccinimide (NHS), N-hydroxysulfosuccinimide (sulfo-NHS), maleimide-benzoyl-succinimide (MBS), gamma-maleimido-butyryloxy succinimide ester (GMBS) and maleimidopropionic acid (MPA). GMBA stands for gamma-maleimide-butrylamide. However, other alcohols, which are functional in an aqueous medium such as blood, may also be employed. In some cases, special reagents find use, such as azido, diazo, carbodiimide anhydride, hydrazine, dialdehydes, thiol groups, or amines to form amides, esters, imines, thioethers, disulfides, substituted amines, or the like. Usually, the covalent bond which is formed should be able to be maintained during the lifetime of the blood component, unless it is intended to be a release site.

The argatroban derivatives are modified so that they covalently react with serum proteins, such as serum albumin or immunoglobulin, or mobile cellular components of the vascular system without loss of antithrombin activity, for systemic treatment of thrombosis. Alternatively, the derivatives covalently react with the surface of an arterial wall, again without loss of antithrombin activity. These derivatives are useful in angioplasty to reduce injury and is envision to be used with or without stent placement to pacify injured vascular regions and to prevent cell adhesion and smooth muscle cell proliferation of the intima, the leading causes of acute reocclusion and restenosis after angioplasty.

The argatroban derivatives are modified so that they covalently react with serum proteins, such as serum albumin or immunoglobulin, or mobile cellular components of the vascular system without loss of antithrombin activity, for systemic treatment of thrombosis. Alternatively, the derivatives covalently react with the surface of an arterial wall, again without loss of antithrombin activity. These derivatives are useful in angioplasty to reduce injury and is envision to be used with or without stent placement to pacify injured vascular regions and to prevent cell adhesion and smooth muscle cell proliferation of the intima, the leading causes of acute reocclusion and restenosis after angioplasty.

The antibodies of the invention may be used in methods for determining the concentration of the argatroban derivatives and conjugates in biological samples (such as blood) using antibodies specific to the argatroban derivatives and conjugates, and to the use of such antibodies as a treatment for toxicity potentially associated with such argatroban derivatives or conjugates. This is advantageous because the increased stability and life of the argatroban derivatives in vivo in the patient might lead to novel problems during treatment, including increased possibility for toxicity. The use of anti-agatroban antibodies, either monoclonal or polyclonal, having specificity for a agatroban derivative thereof, can assist in mediating any such problem. The antibody may be generated or derived from a host immunized with the particular agatroban derivative thereof, or with an immunogenic fragment of the agent, or a synthesized immunogen corresponding to an antigenic determinant of the agent. Preferred antibodies will have high specificity and affinity for derivatized and conjugated forms of the argatroban.

Antibodies specific for derivatized argatroban molecules may be produced by using purified argatroban derivatives for the induction of derivatized argatroban-specific antibodies. By induction of antibodies, it is intended not only the stimulation of an immune response by injection into animals as detailed in the Example section below, but analogous steps in the production of synthetic antibodies or other specific binding molecules such as screening of recombinant immunoglobulin libraries.

The anti-argatroban and argatroban derivative antibodies may be used to treat toxicity induced by administration of the argatroban derivative and may be used ex vivo or in vivo. Ex vivo methods would include immuno-dialysis treatment for toxicity employing anti-agatroban antibodies fixed to solid supports. In vivo methods include administration of anti-argatroban antibodies in amounts effective to induce clearance of antibody-agent complexes.

The antibodies may be used to remove the argatroban derivatives from a patient's blood ex vivo by contacting the blood with the antibodies under sterile conditions. For example, the antibodies can be fixed or otherwise immobilized on a column matrix and the patient's blood can be removed from the patient and passed over the matrix. The argatroban derivatives will bind to the antibodies and the blood containing a low concentration of the argatroban derivative or conjugate, then may be returned to the patient's circulatory system. The amount of argatroban derivative removed can be controlled by adjusting the pressure and flow rate. Preferential removal of argatroban derivatives and conjugates from the plasma component of a patient's blood can be effected, for example, by the use of a semipermeable membrane, or by otherwise first separating the plasma component from the cellular component by ways known in the art prior to passing the plasma component over a matrix containing the anti-therapeutic antibodies. Alternatively the preferential removal of argatroban-conjugated blood cells, including red blood cells, can be effected by collecting and concentrating the blood cells in the patient's blood and contacting those cells with fixed anti-argatroban derivative antibodies to the exclusion of the serum component of the patient's blood.

The anti-argatroban derivative antibodies can be administered in vivo, parenterally, to a patient that has received the argatroban derivatives or conjugates for treatment. The antibodies will bind the argatroban derivative and conjugates. Once bound, the agatroban activity will be hindered if not completely blocked thereby reducing the biologically effective concentration of argatroban derivative in the patient's bloodstream and minimizing harmful side effects. In addition, the bound antibody-argatroban complex will facilitate clearance of the argatroban compounds and conjugates from the patient's blood stream.

The invention also provides kits useful for detecting argatroban and argatroban derivatives. Also provided are kits useful for removing argatroban from the bloodstream. Kits may include reagents for detecting argatroban including Western Blot components, immunochemistry components and flow cytometry reagents. The kits may also include written instructions.

The following examples are presented by way of illustration, not of limitation.

EXAMPLE 1

Synthesis of Argatroban derivatives (1) Argatroban Synthesis

Argatroban is synthesized as follows:

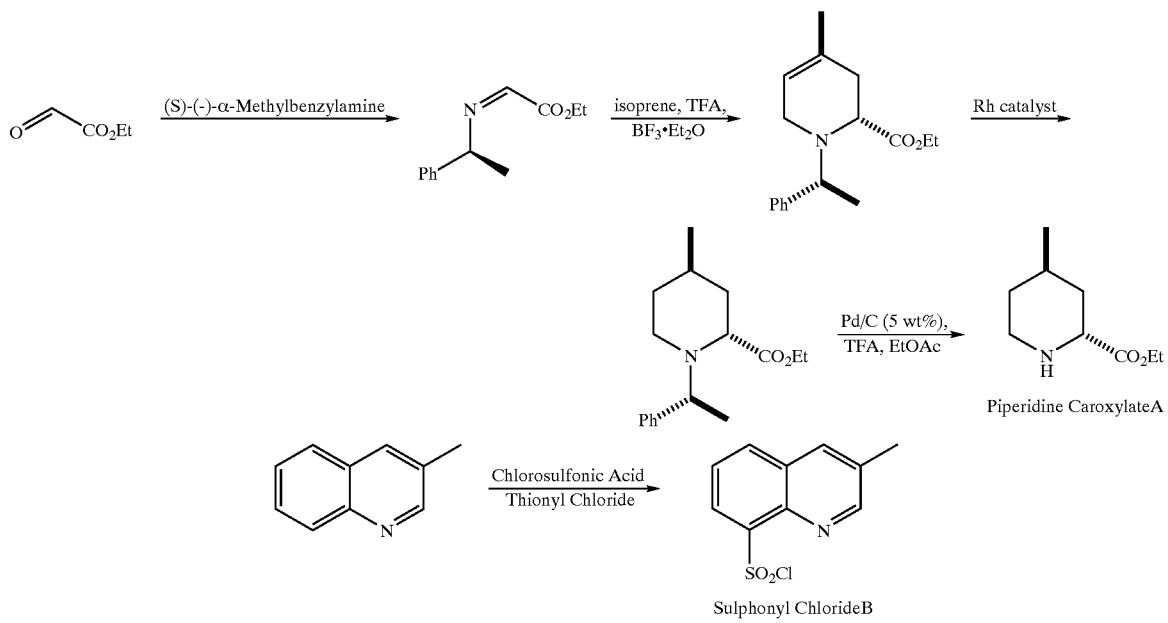

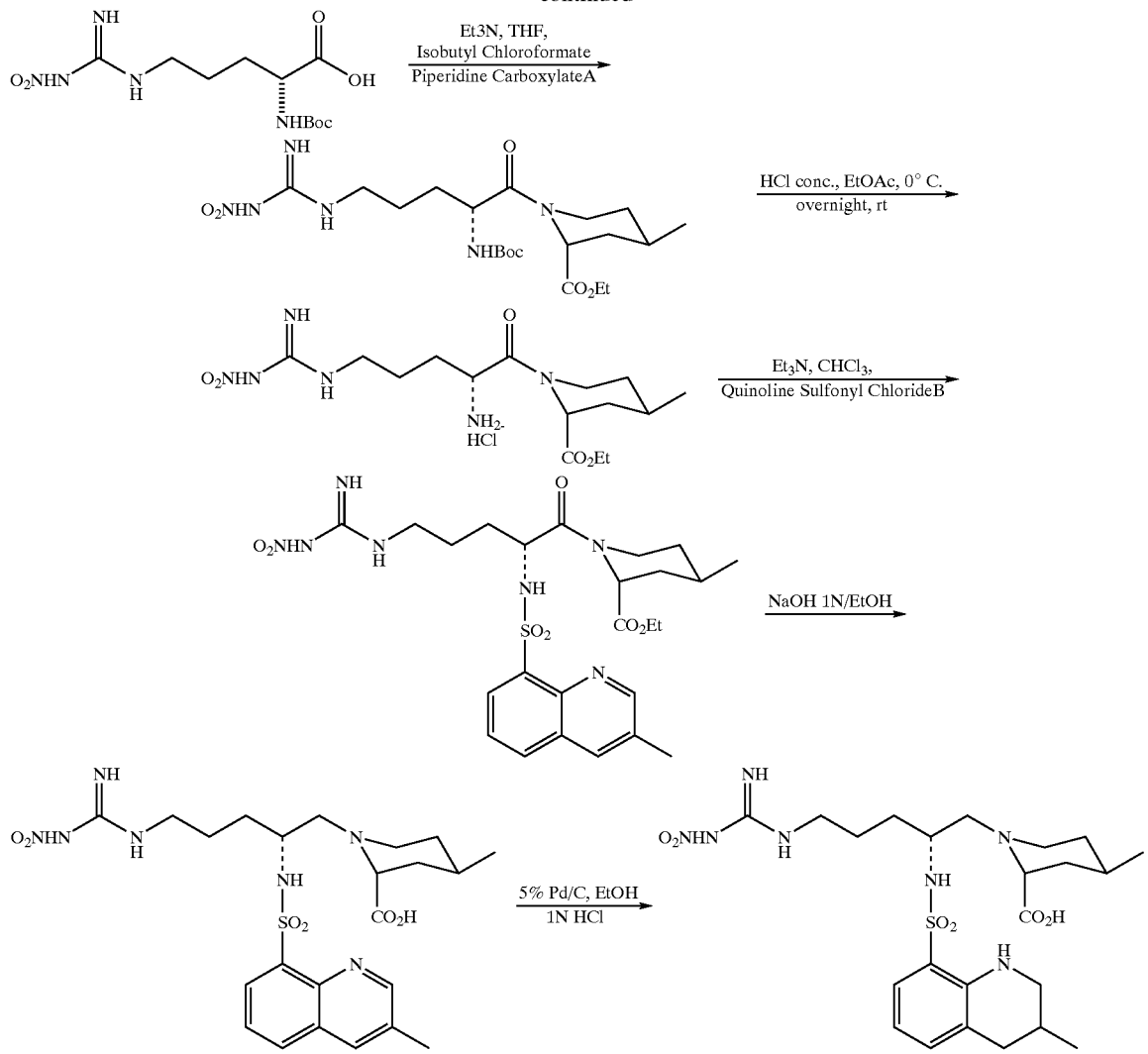

Synthesis of Ethyl [(S)-1-phenylethyl] iminoethanoate

The synthesis was performed according to the procedure reported in the literature. (S)-(−)-α-Methylbenzylamine (238.6 g, 1.964 mol) was added into 2 L round bottom flask equipped a stirrer bar. Toluene (520 mL) was added. The reaction mixture was cooled to −5° C., and was allowed to stir for 10 min. Glyoxylic acid (200 g, 1.96 mol) was tranferred to a dropping funnel and was added slowly to the cooled reaction mixture for approximately 15 min. As the addition of the glyoxylic acid proceeded, the reaction mixture became cloudy and the flask became warm. The mixture was allowed to stir for 10 min after the addition. When the reaction was complete, the water generated during the reaction was removed. The organic layer was dried over $Na_2SO_4$, filtered via Buchner funnel, rinsed with toluene, concentrated in vacuo to yield an oil which was used directly in the next step.

Synthesis of (6R)-1-[(S)-1-phenylethyl]-6-ethoxycarbonyl4-methyl-3,4-didehydropiperidine The synthesis was based on Diels-Alder procedure reported in the literature and was modified in order to obtain a desired product in higher yield. In a 12 L three necked round bottom flask equipped with a thermometer (low temp), overhead stirrer and $N_2$ inlet, the chiral imine obtained in the previous step (402 g, 1.96 mol) and dichloromethane (5.3 L) were added. The reaction mixture was cooled to −70° C. Trifluoro acetic acid (101 mL, 1.31 mol) was added dropwise with stirring via a pressure equalized addition funnel over at least 5 min. During this addition, the internal temperature of the reaction was closely monitored and maintain below −65° C. The mixture was allowed to stir for 10 min. Isoprene (392 mL, 3.92 mol) was added dropwise with stirring via a pressure equalized, dropping funnel over at least 10 min, again maintaining such a rate that the internal temperature did not exceed −65° C. The mixture of $BF_3 \cdot Et_2O$ (250 mL, 1.97 mol) and dichloromethane (0.5 L) were added dropwise (ca 40 min) to the mixture via a fresh pressure equalized addition funnel. The internal temperature was maintained below 65° C. during the 2 5 addition. The reaction mixture was allowed to stir at temperature between −65° C. and −75° C. for 30 min. The reaction was monitored by TLC. When the reaction was complete, the reaction flask was removed from the cooling bath. The saturated solution of sodium carbonate (2 L) was added slowly to the reaction, followed by water (2 L) (pH 8). The aqueous phase was separated, and the organic phase was washed two more times with saturated solution of sodium carbonate (pH of the aqueous phase should eventually end up around 11–12). The combined organic phase was washed with water (4 L), dried over $Na_2SO_4$, filtered via Buchner funnel, rinsed with dichloromethane, concentrated in vacuo to yield an oil. The purification of crude product dissolved in hexane was achieved using a short silica column (600 g) and elution with EtOAc/Hexane (1:9) to give a mixture of 6R/6S. Isolation of (6R) piperidine was achieved by recrystallisation in hexane. The 6R/6S mixture (490 g) was then dissolved in hexane (1L) and the solution was cooled to −78° C. for 1 h. The crystals formed were collected on Buchner funnel, washed with cold hexane to give light yellow solid. Second recrystallisation in cold hexane gave whilte solid as desired product with 99.5% purity (256 g, 50.6 % yield).

Synthesis of (2R, 4R)-1-[(S)-1-phenylethyl]-4-methylpipecolate

The piperidine obtained from previous step (297 g, 1.086 mol), catalyst :[(S)-BINAP]Cl(p-Cymene)RuCl (14.9g, 50 mg/1 g) or (Bicyclo[2.2.1]hepta-2,5-diene)-[1,4-bis(diphenylpgosphino)butane]rhodium(l) tetrafluoroborate (14.9 9, 50 mg/1 g), and ethanol (1.1 L) were added into the hydrogenator. The whole system was purged several times with nitrogen, vacuum, then hydrogen, and sealed. The reaction was allowed to stir at 50° C., 150 Psi $H_2$ (for 12 h. When the reaction was completed, the reaction was allowed to cool to room temperature, then hydrogen was vented from the system. Reaction mixture was concentrated in vacuo to yield dark oil. Purification of the product was achieved using a short silica column (10 g per 1 g) and elution with 2% EtOAc/Hexane. Evaporation of fractions containing product gave colourless oil as pure product.

Synthesis of (2R, 4R)-4-Methylpipecolicolate

Into the hydrogenator, the pipecolate obtained above (242g, 0.897 mol) was dissolved in EtOAc (500 mL). Trifluoroacetic acid (77 mL) was added dropwise with stirring. The palladium catalyst (1.8 g) was added portionwise with extreme caution. Upon the complete addition, the reactor was purged several times with $N_2$, vacuum, and hydrogen, and sealed. The reaction was allowed to stir at room temp, 150 Psi $H_2$ for 1 h. Hydrogen was vented from the system. The reaction mixture was transferred into the extraction funnel, diluted with EtOAc (1L), washed three times with saturated solution of $Na_2CO_3$ (500 mL). After the last washing, the pH of the aqueous phase should be at 11. The combined organic phase was dried over $Na_2SO_4$, filtered via Buchner funnel, rinsed with ethyl acetate, concentrated in vacuo to yield an oil as piperidine carboxyalte A.

Synthesis of 3-methyl 8-sulfonyl Chloride Quinoline

Into 2L round bottom flask equipped with $N_2$ inlet, Chlorosulfonic acid (486 mL) was added. The reaction mixture was cooled to −5° C. 3-methyl quinoline (270 g, 1.89 mol) was added slowly with stirring via a pressure equalized dropping funnel . When the addition was complete, the cooling bath was removed, and the reaction mixture was allowed to stir at room temperature for at least 30 min until all solids dissolved. The funnel was replaced with a reflux condensor and a guard tube. The reaction mixture was then heated to reflux for 5 h. A vigourous reaction with gas evolution can occur at this stage so due care and diligence should be observed. The reaction mixture was cool to −5° C. with an ice bath, and the guard tube was replaced with $N_2$ inlet. The reflux condensor was replaced by a pressure equalized dropping funnel charged with thionyl chloride (179 mL, 2.45 mol). Thionyl Chloride was added dropwise over at least 1 h. When the addition was complete, the cooling bath was removed and the reaction mixture was allowed to stir for 30 min at room temp. The reaction mixture was heated to reflux with stirring for 2 h. The reaction mixture was allowed to cool down to room temp and was poured slowly onto the ice/water bath prepared from 2 L of ice. The aqueous mixture was extracted five times with dichloromethane (1L). The combined organic phase was washed with saturated solution of $Na_2CO_3$ (1 L), then with water (1 L). The combined organic phase was dried over $Na_2SO_4$, filtered via Buchner funnel, rinsed with dichloromethane, concentrated in vacuo to yield 3-methyl 8-sulfonyl chloride quinoline B.

(2) Synthesis of Argatroban-C6-NHS

Manufacture of Argatroban-C6-NHS from Argatroban.2HCl

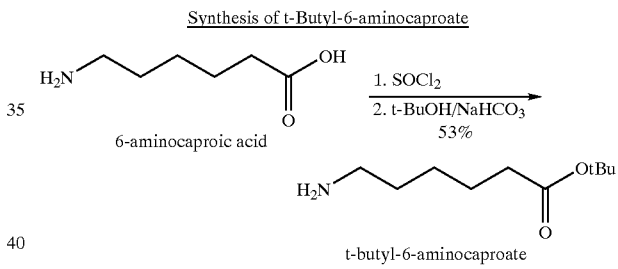

In a 10 L reaction flask equipped with $N_2$ inlet, 0.383 Kg of 6-aminocaproic acid (2.92 mol) was slowly added to 3.14 Kg of stirring thionyl chloride (26.28 mol). The maximum temperature during the addition is kept at about 30° C. Upon complete addition, the reaction was allowed to stir at 20–30° C. for 1 h, then concentrated via rotary evaporation (max 40° C. bath). Excess thionyl chloride was chased-off by the addition of toluene (0.843 Kg) and the solution was re-concentrated via rotary evaporation (max 40° C. bath). To the resulting tan solid a suspension of 0.537 Kg of sodium bicarbonate (6.42 mol) was added in 2.97 Kg of t-BuOH (40.3 mol) and reaction allowed to stir at 20–30° C. for 2 h. The excess t-BuOH was removed in vacuo (max 40° C. bath) and residue diluted with 5.17 Kg of ethyl acetate and washed with four portions of 1M NaOH (0.307 Kg in 7.68 Kg water), three portions of $H_2O$ (1.92 Kg), one portion of sat. aq. NaCl (0.767 Kg in 1.92 Kg water), dried with anhydrous $Na_2SO_4$ (0.383 Kg), filtered via Buchner funnel, rinced with ethyl acetate (1.72 Kg), and concentrated in vacuo (max 50° C. bath). The tan liquid residue was distilled (bp 97–98° C./2 mmHg) to afford 0.290 Kg of t-butyl-6-aminocaproate (53% yld) as a clear colourless to light yellow oil.

Synthesis of Argatroban-C6-COOH Dihydrochloride Salt (Arg-C6-COOH-2HCl)

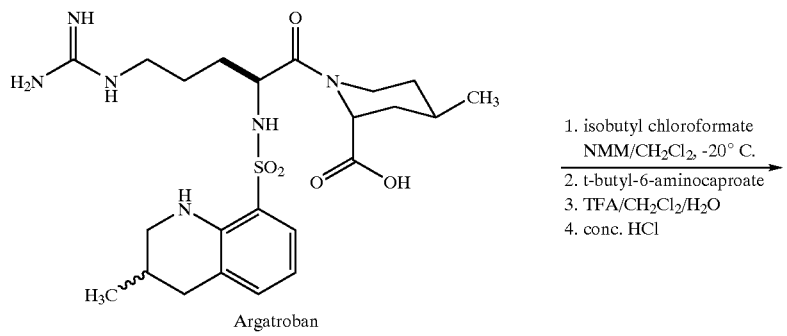

Argatroban 1. isobutyl chloroformate NMM/CH$_2$Cl$_2$, -20° C.
2. t-butyl-6-aminocaproate
3. TFA/CH$_2$Cl$_2$/H$_2$O
4. conc. HCl

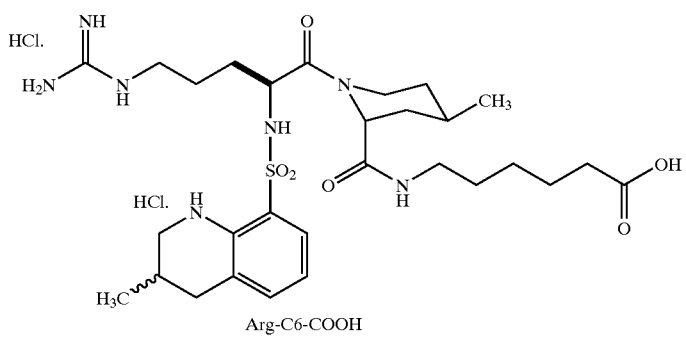

Arg-C6-COOH

In a 20 L flask equipped with N$_2$ inlet, 0.100 Kg of Argatroban.2HCl (0.172 mol) was added. Dichloromethane (6.6 Kg) was added. N-methylmorpholine (0.070 Kg, 0.688 mol) was added with strong agitation This solution was cooled to −20° C. (−23° C. to −17° C.), and the agitation was continued until all solids dissolve. Isobutyl chloroformate (0.070 Kg, 0.688 mol) was added while keeping the reaction temperature at −20° C. The reaction mixture was allowed to stir for 10–20 min. To this mixture, t-butyl-6-aminocaproate (0.097 Kg, 0.516 mol) was added, and the resulting clear solution was allowed to stir for 1.0 h while slowly warming to RT. This mixture was cooled to −20° C., and repeat the addition of N-methylmorpholine (0.018 Kg, 0.172 mol), Isobutyl chloroformate (0.018 Kg, 0.172 mol), t-butyl-6-aminocaproate (0.032 Kg, 0.172 mol).

The reaction was followed by TLC and HPLC. When the reaction was finished, dichloromethane (6.6 Kg) was added. The organic layer was washed twice with mixture of NaCl/water/HCl (0.60 Kg/ 10 Kg/ 0.31 Kg). The combined organic phase was washed once with NaCl solution (5.0 Kg water/ 0.30 Kg NaCl), dried with anhydrous Na$_2$SO$_4$ (0.69 Kg), filtered via Buchner funnel, rinced with dichloromethane (3.4 Kg), and concentrated into 20 L rotavap flask to dryness in vacuo (max 25° C. bath). The trace of solvent was chased-off by the addition of diethyl ether and the solution was re-concentrated via rotary evaporation (max 250° C. bath). Dichloromethane (0.58 Kg), water (0.12 Kg) were added to the residue. Trifluoroacetic acid (1.4 Kg) was added slowly with strong agitation. The reaction mixture was allowed to stir at 22° C. until the reaction was completed (1 h). The reaction was followed by HPLC. The reaction mixture was concentrated (not to dryness) in vacuo (max 25° C. bath). Dichloromethane (2.3 Kg) was added into the concentrated mixture. The pH of the mixture was adjusted to 11–13 with aqueous NaOH(0.20 Kg NaOH/5.0 Kg water) with caustic while maintaining the room temp. The layers were separated, and the organic layers were extracted with caustic once again (0.036 Kg NaOH/0.90 Kg water). The aqueous layers were combined and washed further with dichloromethane (3.4 Kg). The aqueous mixture was acidified to pH 1 or less with conc. HCl (0.3 Kg) with caustic while maintaining the room temp. The mixture was extracted three times with ethyl acetate (2.3 Kg). The organic layers were combined, dried over anhydrous Na$_2$SO$_4$ (0.52 Kg), filtered via Buchner funnel, rinced with ethyl acetate (1.0 Kg), and concentrated into 20 L rotavap flask to dryness in vacuo (max 25° C. bath). The trace of ethyl acetate was chased-off by the addition of diethyl ether and the solution was re-concentrated via rotary evaporation (max 250° C. bath) to afford the crude Arg-C6-COOH as a white solid (more than 90% purity). This material was used into the next step without purification.

Synthesis of Argatroban-C6-NHS Ester Dihydrochloride Salt (Arg-C6-NHS)

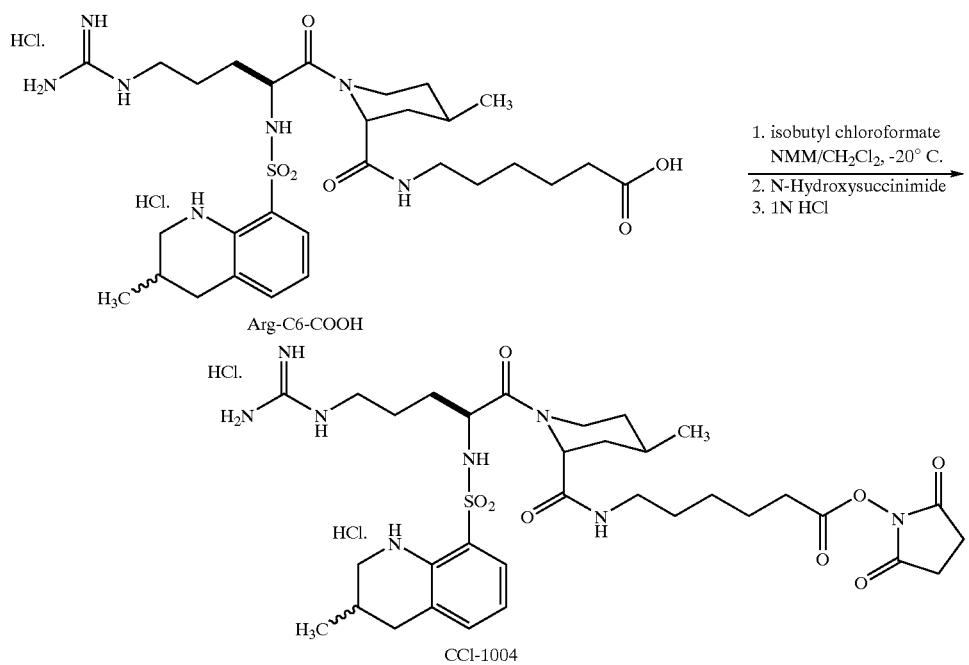

In a 250 mL flask equipped with magnetic stir bar and $N_2$ inlet, Arg-C6-COOH (1 g, 0.00144 mol) was dissolved in 70 mL $CH_2Cl_2$. N-methylmorpholine (1.46 g, 0.0144 mol) was added at room temp. The mixture was allowed to stir at room temp until all solids dissolve. This solution was cooled to −20° C. (−23° C. to −17° C.), with strong agitation 2 mL of TFA, and 0.25 mL of $H_2O$ and the reaction mixture allowed to stir at RT for 40 min. The mixture was then concentrated in vacuo to afford 62.0 mg of crude argatroban-C6-acid as a colorless film (product is a single peak by analytical HPLC, method described in the physicochemical section). This crude material was then dissolved in 2 mL of dry N,N-dimethylformamide and 58.6 µL of N-methylmorpholine (0.533 mmol). This solution was cooled to −20° C. and stirred for 10 min. Isobutyl chloroformate (0.98 g, 0.0072 mol) was added in a single portion and reaction allowed to stir for 20 min at −20° C. To this reaction mixture was added N-hydroxysuccinimide (0.828 g, 0.0072 mol) and allowed to stir for 20 min at −20° C. while slowly warming to ambient temperature ca 1 h. To the clear solution 1N HCl (100 mL), solution of saturated NaCl (50 mL) were added. The layers were separated, and the organic layer was washed with saturated solution of NaCl (50 mL), dried over anhydrous $Na_2SO_4$, filtered via Buchner funnel, rinced with dichloromethane, and concentrated to dryness in vacuo (max 25° C. bath). Crude reaction product (1.4 g) was purified using a Biotage column (40M) pressurized at 30 Psi $N_2$. The column was initially washed with 300 mL of EtOAc/EtOH/0.1N HCl, 80/20/2 and eluted with the same eluant. Evaporation of the 10 mL fractions containing the product (60–100) gave yellowish oil. The trace of solvent was chased-off by the addition twice of diethyl ether (50 mL) and the solution was re-concentrated via rotary evaporation (max 25° C. bath) to afford CCI-1004 with 96.9% purity (by LC/MS) (0.80 g, 58% yield).

(3) Synthesis of Argatroban C13-Maleimide

The synthesis of Arg C13-Maleimide is according to the method described below as outlined in FIG. 1.

Compounds YS-41-31 and YS-41-33. To a solution of 3-maleimidopropionic acid (100 mg, 0.592 mmol), HOBt (88 mg, 0.652 mmol) in $CH_2Cl_2$ (5 mQ, DCC (134 mg, 0.650 mmol) was added. The mixture was stirred at room temperature for 1 h. A solution of t-butyl 6-aminohexyl carbonate hydrochloride (165 mg, 0.653 mmol) and triethylamine (0.100 mL, 0.719 mmol) in anhydrous DMF (5 mL) was added. The reaction mixture was stirred at room temperature overnight. It was filtered, and the filtrate was concentrated in vacuo. The residue was dissolved in $CH_2Cl_2$. The solution was washed with 5% $NaHCO_3$, 10% $KHSO_4$ and water. It was dried over $Na_2SO_4$, concentrated in vacuo to give an amorphous solid (173 mg) (YS-41-31) (yield: 79%).

The solid (125 mg) was dissolved in TFA (5 mL). The solution was allowed to stand at room temperature for 1.5 h. TFA was removed in vacuo. The residue was dissolved in $CH_3CN$ (2 mL), then water (15 mL) was added. The solution was lyophilized to give an amorphous solid (130 mg) (YS-41-33) (yield: 99%)

Compound YS41-37. To a solution of argatroban monohydrate (167 mg. 0.317 mmol) and compound YS41-33 (133 mg, 0.349 mmol) in anhydrous DMF (5 mL), triethylamine (58 µL, 0.417 mmol) was added, followed by addition of HBTU (144 mg, 0.380 mmol). The mixture was stirred at room temperature for 8 h. TLC showed a new bright spot. DMF was removed in vacuo, and the residue was purified by HPLC using a gradient of $CH_3CN$ in $H_2O$ containing 0.045% TFA from 10% to 100% over 55 min., to afford a white powder (103 mg) (YS41-37) (yield: 37%).

(4) Synthesis of Argatroban-C21-PE-Maleimide

Figure 2:
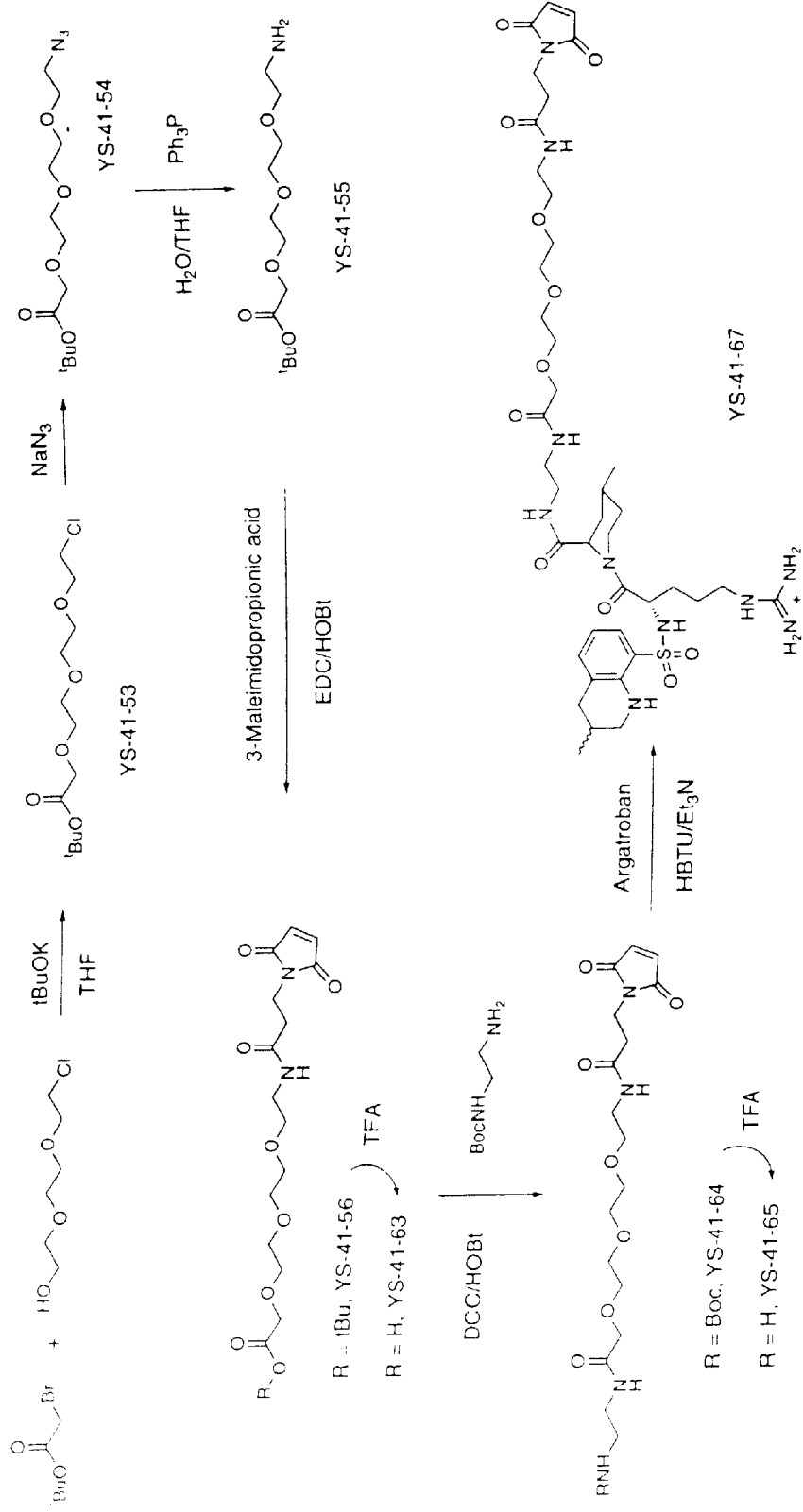
FIG. 2 is a schematic showing the synthesis of argatroban C21-PE-maleimide.

The synthesis of Arg C21-PE-Mal is according to the method described below as outlined in FIG. 2.

Compound YS-41-53.

The method of synthesis includes the steps of to a solution of 2-[2-(2-chloroethoxy)ethoxy]ethanol (1.69 g, 10 mmol)

and t-butyl bromoacetate (1.95 g, 10 mmol) in anhydrous THF (22 mL), potassium t-butoxide (L 18 g, 95%, 10 mmol). The mixture was stirred at room temperature overnight. Water and ethyl acetate were added. Organic phase was separated, and aqueous phase was extracted with ethyl acetate. The combined organic solutions were dried over $Na_2SO_4$, then concentrated in vacuo to give a brownish liquid, which was purified by flash column using solvents EtOAc/hexanes (30 M) to afford a clear liquid (0.95 g) (YS-41-53) (yield: 33%).

Compound YS-41-54. To a solution of the chloride YS-41-53 (0.92 g, 3.26 mmol) in anhydrous DMF (30 mL), sodium azide (1.04 g, 16 mmol) was added. The suspension was then heated to 80° C. overnight. Ethyl acetate was added and the solution was washed with $H_2O$. The organic phase was dried over $Na_2SO_4$, concentrated in vacuo to give a yellowish liquid (0.90 g) (YS-41-54) (yield: 96%).

Compound YS-41-55. To a solution of the azide YS-41-54 (0.461 g, 1.60 mmol) in THF (2.5 mL), triphenylphosphine (0.463 g, 1.77 mmol) and water (43 µL, 2.39 mmol) were added. The mixture was stirred at room temperature overnight. The solution was concentrated in vacuo, and the residue was purified by a flash column using solvents $CH_3OH/CH_2Cl_2$ (30/70) to afford a yellowish liquid (0.34 g) (YS41-55) (yield: 81%).

Compounds YS-41-56 and YS-41-63. To a solution of 3-maleimidopropionic acid (100 mg, 0.592 mmol), HOBt (88 mg, 0.652 mmol) in $CH_2Cl_2$ (5 mL), EDC (126 mg, 0.657 mmol) was added. The mixture was stirred at room temperature for 30 min. A solution of the amino acid YS-41-55 (156 mg, 0.593 mmol) in $CH_2Cl_2$ (2 mL) was added. The reaction mixture was stiffed at room temperature overnight. The solution was concentrated in vacuo, and the residue was purified by a flash column using solvents $CH_2Cl_2/CH_3OH$ (95/5) to afford an oil (214 mg) (YS-41-56) (yield: 87%).

The oil (86 mg, 0.208 mmol) was dissolved in TFA (3 mL). The solution was allowed to stand at room temperature for 1 h. TFA was removed in vacuo, and the residue was dissolved in $H_2O$. The aqueous solution was Iyophilized to give an oil (85 mg) (YS41-63) (Yield: quantitative).

Compounds YS-41-64 and YS-41-65. To a solution of the acid YS-41-63 (80 mg, 0.223 mmol) and HOBt (45 mg, 0.333 mmol) in $CH_2O2$ (4 mL), DCC (69 mg, 0.335 mmol) was added. Stiffing was continued at room temperature for 30 min. A solution of N-Boc ethanediamine (54 mg, 0.338 mmol) in $CH_2Cl_2$ (2 mL) was added. The mixture was stiffed at room temperature overnight. The solution was filtered, and the filtrate was applied to a silica gel column, which was eluted with $CH_2Cl_2/CH_3OH$ (92/8) to afford compound YS41-64 (56 mg) (yield: 50%).

Compound YS-41-64 (56 mg, 0.112 mmol) was dissolved in TFA (3 mQ. The solution was allowed to stand at room temperature for 1.5 h. TFA was removed in vacuo, the residue was dissolved in $H_2O$. The aqueous solution was then lyophilized to give an oil (62 mg) (YS-41-65) (yield: quantitative).

Compound YS-41-67. To a solution of argatroban hydrate (57 mg, 0.108 mmol) and the amine YS- 41-65 (56 mg, 0.109 mmol) in anhydrous DMF (3 mL), triethylamine (20 µL, 0.144 mmol) was added, followed by addition of HBTU (49 mg, 0.129 mmol). The mixture was stiffed at room temperature overnight. TLC showed that there was still considerable amount of unreacted argatroban remaining. Therefore, more HBTU (28 mg, 0.074 mmol) was added. Stirring was continued for another 2 h. DMF was removed in vacuo, the residue was purified by HPLC using a gradient of $CH_3CN$ in $H_2O$ containing 0.045% TFA from 10% to 100% over 55 min., to afford a white powder (29 mg) (YS-41 67) (yield: 27%). The material was water soluble.

(5) Synthesis of Argatroban C18-Maleimide

Figure 3:
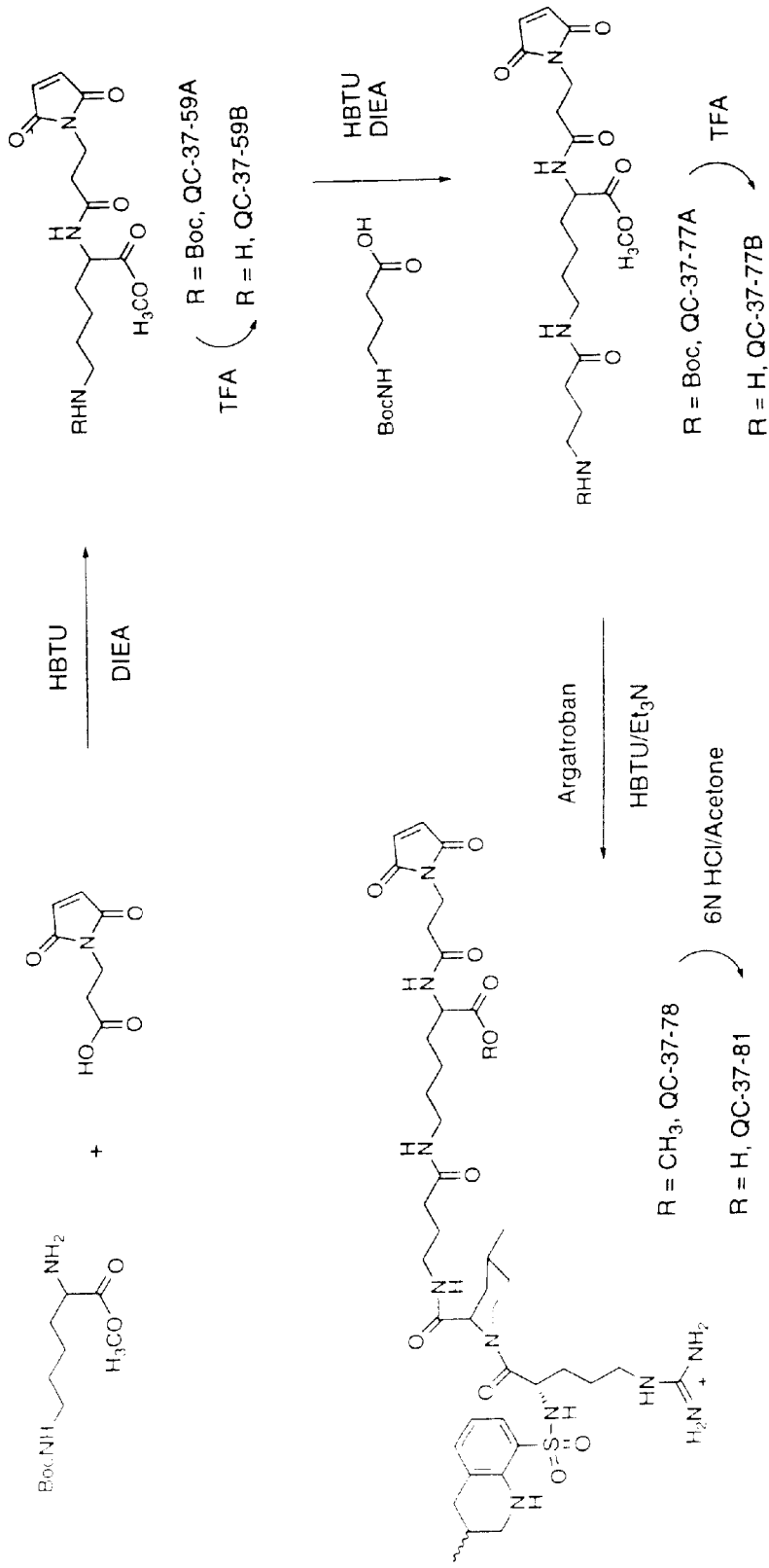
FIG. 3 is a schematic showing the synthesis of argatroban C18 maleimide.

The synthesis of Arg C18-Mal is according to the method described below as outlined in FIG. 3.

Compounds QC-37-59A and OC-37-59B. To a solution of maleimidopropionic acid (1.00 g, 5.91 mmol) and Nε-Boc lysine methyl ester (1.93 g, 6.50 mmol) in DMF (10 mL), HBTU (2.46 g, 6.50 mmol) and DIEA (1.52 g, 11.82 mmol) were added. The solution was stirred at room temperature overnight. DMF was removed in vacuo. The residue was dissolved in $CH_2Cl_2$. It was washed with 5% $NaHCO_3$, $H_2O$, 10% $KHSO_4$, $H_2O$, dried over $MgSO_4$, concentrated in vacuo. The residue was purified by a flash column using solvents $CH_2Cl_2/CH_3OH$ (95/5) to give compound QC-37-59A (1.43 g) (yield: 59%).

Compound QG-37-59A (1.43 g, 3.48 mmol) was dissolved in TFA (10 ML). The solution was allowed to stand at room temperature for 1.5 h. TFA was removed in vacuo, the residue was dissolved in $H_2O$. The aqueous solution was then lyophilized to give an oil (1.50 9) (QC-37-59B) (yield: quantitative).

Compounds OC-37-77A and QC-37-77B. To a solution of compound QC-37-59B (0.935 g, 2.20 mmol) and N-Boc γ-aminobutyric acid (0.471 g, 2.32 mimol) in DMF (7 mL), HBTU (0.879 g, 2.32 mmol) and DEEA (0.545 g, 4.22 mmol) were added. Stiffing was continued at room temperature overnight. DMF was removed in vacuo, the residue was dissolved in $CH_2O_2$. The solution was filtered, concentrated in vacuo. The crude product was purified by a flash column using solvents $CH_2Cl_2/CH_3OH$ (95/5) to afford compound QC-37-77A (0.482 g) (yield: 44%).

Compound QC-37-77A (0.300 g, 0.605 mmol) was dissolved in TFA (4 mL). The solution was allowed to stand at room temperature for 1.5 h. TFA was removed in vacuo, the residue was dissolved in $H_2O$. The aqueous solution was then lyophilized to give an oil (0.310 g) (QC-37-77B) (yield: quantitative).

Compound OC-37-78. To a solution of argatroban hydrate (200 mg, 0.379 mmol), compound QC-37-77B (240 mg, 0.471 mmol) in DMF (8 mL), HBTU (172 mg, 0.455 mmol) and triethylarnine (76.6 mg, 0.758 mmol) were added. The mixture was stirred at room temperature overnight. DMF was removed in vacuo, the residue was purified by HPLC using a gradient of $CH_3CN$ in $H_2O$ containing 0.045% TFA from 10% to 100% over 55 min., to afford a white powder (129 mg) (QC-37-78) (yield: 38%).

Compound QC-37-81. To a solution of compound QC-37-78 (9.1 mg, 10.3 µmol) in acetone (1 mL), aqueous HCl (6N, 2 mL) was added. The mixture was stirred at room temperature overnight. Solvents were removed in vacuo, the residue was purified by HPLC using a gradient of $CH_3CN$ in $H_2O$ containing 0.045% TFA from 10% to 100% over 55 min., to afford a white powder (4.2 mg) (QC-37-81) (yield: 47%).

EXAMPLE 2

Preparation of Immunouen

An argatroban immunogen was prepared by conjugating argatroban to keyhole limpet hemocyanin (KLH) for a final concentration of 2 mg KLH/ml in PBS, 1% DMSO, 3.5% ethanol. 10 µl of Argatroban-C6-NHS (3 mg, DMSO), prepared as above in Example 1, was added to 200 µl of KLH (10 mg/ml) and 790 µ phosphate-buffered saline (PBS), pH 7.4. 35 µl ethanol was added to improve solubility, and the solution was incubated at 25° C. for 1 hour. The reaction was quenched by the addition of 50 µl 1M hydroxylamine at room temperature of 10 minutes, and the resulting conjugate was stored at −20° C.

EXAMPLE 3

Control Analysis of Immunogen

The immunogen of Example 2 was assessed by a capture ELISA. Microtiter plates were coated with anti-KLH antibody (5 µg/ml, 1:5000) and washed with PBS. Dilutions of argatroban-KLH conjugate ranging from 0–20,0000 µg/ml in PBS-1% BSA were added to wells of the microtiter plates (100 µl/well) and allowed to incubate at room temperature for 2 hrs. Identical dilutions of KLH alone were added to other wells of the plates as a control. After washing with PBS, 100 µl /well thrombin (9.1 µg/ml, PBS-1% BSA-0.1% PEG 6000) was added to each well and allowed to incubate at room temperature for 1 hour. The plates were again washed in PBS and rabbit anti-thrombin antibody (Am. Diag., 1 µg/ml, 1:1000 dilution in PBS-1% BSA-0.1% PEG 6000) was added and incubated for 30 min. at room temperature. The plates were again washed with PBS and biotinylated goat anti-rabbit IgG antibody was added (Vector, 1:1000 dilution in PBS-0.1% BSA-0. 10% PEG 6000) and incubated for 30 minutes at room temperature, followed by the addition of an streptavidin-horseradish peroxidase (streptavidin-HRP) conjugate (Vector, 1:500 dilution in PBS-0.1% BSA-0.1% PEG 6000) and incubation for an additional 30 minutes. After washing again in PBS, 100 µl/well of orthophenyldiamine (OPD) (0.5 mg/ml) was added, incubated for 30 min at room temperature. The reaction was quenched by the addition of 100 µl/well 2 N sulfuric acid, and the plates were read at OD 490 nm.

Strong signal of greater than 1.0 was observed at concentrations of argatroban-KLH as low as 1000 ng/ml, indicating argatroban was efficiently conjugated to the KLH. The control wells gave no visible signal.

EXAMPLE 4

Immunization of Rabbits

The immunogen of Example 2 was emulsified in complete Freunds adjuvant (CFA) and injected subcutaneously into New Zealand rabbits (rabbits 96019 and 96020) at 200 µg of immunogen per animal. Subsequent immunizations were performed at three week intervals using 200 µg/rabbit of immunogen emulsified in Freunds incomplete adjuvant (IFA), again injected subcutaneously, for a three month period. Sera was collected at seven days following the third and fourth immunizations and upon exsanguination at seven days following the fifth and final immunization.

EXAMPLE 5

Antibody Detection

Serum collected from the immunized rabbits of Example 4 (rabbits 96019 and 96020) was tested for anti-argatroban antibodies capture ELISA using Argatroban-gelatin conjugates as coating antigens. Briefly, microplates (NUNC maxisorp) were saturated with PBS containing 1% gelatin (100 µl/well) for 1 hour at 37° C., washed with PBS, incubated for 1 hour at 37° C. with NHS-Argatroban (batch YS-004-89-02) at 10 µM in PBS, washed with PBS+0.05% Tween 20 (PBST), saturated again by gelatin, and finally washed with PBST. Serum samples collected from rabbits 96019 and 96020 and diluted in PBST was incubated for 1 hour at 37° C. The serum samples included samples taken prior to immunization, and samples collected after the third and fourth immunizations. After 3 washes with PBST, bound antibodies were incubated for 1 hour at 37° C. with anti-rabbit IgG(H+L) conjugated to phosphatase (BioAtlantic, France) diluted 1/2,000 in PBST. After washing, pNPP (4 mg/ml) was added, incubated for 30 min at 37° C., and the plates were read at OD 405 nm.

Antisera from both rabbits 96019 and 96020 showed high titer to argatroban as measured by the ELISA results, yielding absorptions at OD 405 nm of at least 2.0 at dilutions of 1:16,000 and greater. Preimmune sera taken from the rabbits prior to immunization gave no signal at such dilutions.

EXAMPLE 6

Purification and Labeling of Anti-argatroban Antibodies

Polyclonal antibodies from the sera collected from the immunized rabbits 96019 and 96020 of Example 4 was purified using affinity chromatography on an ovalbumin-argatroban column and labelled with either biotin, horseradish peroxidase (HRP), or fluorescein isothiocyanate (FITC).

Affinity purification and biotin, peroxidase and FITC labelling

Polyclonal antibodies were purified from antisera by affinity chromatography. The affinity column was prepared by coupling argatroban-C6-NHS, prepared as above in example 1, to ovalbumin. The ovalbumin-argatroban conjugate was then coupled to a Sepharose gel activated by cyanogen bromide. The antisera was diluted in binding buffer and loaded on the column. Bound antibodies were then eluted with an elution buffer, neutralized and stored for further processing.

The purified antibodies were labelled by standard methods with either biotin, peroxidase or FITC, and their reactivity to argatroban-red blood cells was tested. The biotin-labelled and the peroxidase-labelled antibodies recognized argatroban-protein conjugates by ELISA, and the FITC-labelled antibodies recognized argatroban-red blood cells in flow cytometry assays.

EXAMPLE 7

Detection of in vitro Anchored Arcatroban to Plasma Proteins and Red Blood Cells A. In vitro anchoring to blood proteins and cells Whole blood samples were treated with argatroban derivatives to yield plasma proteins and red blood cells derivatized with argatroban. Fresh citrated human, rabbit (New Zealand) and rat (Sprague Dawley) whole blood samples were incubated with 100 µM (final concentration) Argatroban-C6-NHS, Argatroban-C16-Maleimide or DMSO, for 30 minutes at room temperature under gentle agitation. After quenching the reaction with 1 mM lysine or cysteine, the whole blood was centrifuged 10 min at 2500 rpm. Labelled plasma were recovered and stored at −20° C. until use. Labelled red blood cells (RBCs) were washed three times in PBS (5 min at 2500 rpm).

B. Western-blot:

Labeled plasma were diluted 1/10 in water. Five μl of diluted plasma (·30 μg protein) were mixed with electrophoresis buffer and separated by SDS-PAGE using an 8% polyacrylamide gel, under non-reducing conditions. Plasma proteins were then transferred onto nitrocellulose sheet with a semi-dry transfer apparatus. Efficacy of transfer was checked by reversible staining with 1% Ponceau Red. The blot was saturated with tris-buffered saline (TBS) containing 5% gelatin and 0.1% Tween 20, for 2H at 37° C. to minimize non-specific binding. After three washes with TBS-1 % Tween 20 (TBS-T), the blot was incubated with rabbit anti-argatroban polyclonal serum from diluted 1/20,000 in TBS containing 1% gelatin and 0.1% Tween 20 (TBS-GT), for 1H30 at RT. The blot was washed three times with TBS-T, for 10 minutes and then incubated with peroxidase-labeled goat anti-rabbit 1 g (Sigma A0545) diluted 1/200,000 in TBS-GT, for 1 hour at room temperature. After three washes with TBS-T, development was performed using the ECL method (Amersham) with a 3 minute exposure.

The results of the Western blot indicate that the anti-argatroban antibodies recognize and bind the derivatized plasma proteins. Numerous protein bands in both the human and rat derivatized samples, ranging from less than 39.5 kDa to greater than 193 kDa were identified for both the argatroban-NHS derivatized samples and the argatroban-maleimide derivitized samples. Corresponding samples incubated with DMSO yielded bands only in the 112–193 kDa range human and 193 kDa range for rat due to the non specific interactions with the second antibody. The rabbit derivatized samples yielded a wide range of protein bands for all three samples (argatroban-NHS, argatroban-maleimide and DMSO) likely due to non-specific interactions between the rabbit plasma proteins and the anti-rabbit labelling agent.

C. Flow cytometry

After the last centrifugation, a 10% suspension of labelled red blood cells (RBCS) was made in PBS. Five μl of the suspension was mixed with rabbit anti-argatroban polyclonal sera from Example 4 diluted 1/500 in PBS-1% BSA and incubated at room temperature for 1 hour. After three washes in PBS, the RBCs were incubated with 50 μl of FITC-labeled goat anti-rabbit Ig (BioAtlantic, Nantes) diluted 1/50 in PBS-1% BSA for 1 hour in the dark. After three washes, the RBCs were resuspended in 0.5 ml PBS and fluorescence was detected by flow cytofluorometer (Becton Dickinson).

For each sample, the mean fluorescence was highest for the argatroban-NHS derivatized cells, giving signals approximately 3 to 7 times stronger than the argatroban-maleimide derivatized cells. This difference may be due to the differential between the availability of amine groups on RBCs for covalent bonding as compared to the availability of sulfhydryl groups. The DMSO treated cells gave no appreciable signal.

EXAMPLE 8

Detection of In Vitro Anchored Argatroban to Human Serum Albumin

A. Preparation of HSA-argatroban conjugates:

Several argatroban derivatives were mixed with 40 mg/ml solution of human serum albumin (HSA) (Calbiochem) in PBS (=600 μM) at a molar ratio of 1:1 (1 argatroban molecule per 1 albumin molecule). The reactions were allowed to proceed for 1 hour at 37° C., and then the unconjugated argatroban material was removed by loading the samples on a desalting column (Econo-pac, BioRad) previously equilibrated in PBS. Proteins were eluted with PBS in 500 l fractions, and the concentration of collected fractions was estimated by the bicinchoninic acid (BCA) method (BCA kit, Pierce). Fractions containing HSA were pooled and the protein concentration was again estimated using BCA. HSA-argatroban conjugates were stored at 4 C for short term or −20° C. for long term.

B. ELISA:

A 96-well microplate (NUNC, Maxisorp) was incubated with mouse monoclonal anti-HSA antibody (Pierce) diluted at 2 μg/ml in PBS, 100 μl/well, overnight at 4° C. The plate was washed twice in PBS and was saturated with PBS-1 % BSA, 200 l/well, and incubated for 2 hours at room temperature. After three washes with PBS-0.05% Tween 20 (PBS-T), HSA-argatroban conjugates diluted in PBS-1 % BSA were added (100 μl per well) and incubated for 2 hours at room temperature. The plate was washed 3 times with PBS-T and was incubated with rabbit anti-argatroban polyclonal sera generated in Example 4, diluted 1/1000 with PBS-1 % BSA, for 1 hour at room temperature. After 3 washes, the plate was incubated with peroxidase-labeled goat anti-rabbit IgG (Jackson) diluted 1/10,000 in PBS-1 % BSA for 1 hour at room temperature in the dark. After 3 washes, detection captured HSA-argatroban was performed by adding 100μl of 0.5 mg/ml ortho-phenylenediamine (OPD) in citrate-phosphate buffer containing $H_2O_2$, and incubating for 15 minutes in the dark. The reaction was stopped with 50 μl of 2N $H_2SO_4$ and plate was read at 492 nm.

Detection of captured HSA-argatroban was observed at HSA concentrations as low as approximately 40 ng/ml of HSA, for the NHS- and maleimide-derivatized HSA.

Alternatively, argatroban conjugated to albumin or to other plasma protein can be detected directly by coating the proteins to the plate without the use of a protein-specific capture antibody. In either case, the advantage of such detection methods is that only proteins conjugated to argatroban can be detected, as free argatroban is not adsorbed to the plate.

EXAMPLE 9

Detection of In Vivo Anchored Argatroban to Rat Plasma Protein

A. In vivo experiments in rats:

Fifteen Sprague-Dawley rats weighing 250–300 grams were randomized for treatment with either argatroban and argatroban derivative. Rats treated with argatroban received dosages of either 3 or 10 mg/kg (n=6 and respectively) administered intravenously. Rats treated with argatroban derivatives (C6-NHS; YS-41-38) received dosages of 10 mg/kg intravenously (n=4). A control group of rats was treated with intravenous injection of DMSO (0.2 ml/kg, n=3). The study was divided into two groups. Plasma samples were obtained from group 1 rats at time periods of 5 min, 15 min, and 24 hrs after injection. Plasma samples were obtained from group 2 rats at 1 hr, 3 hr and 24 hr following injection. At selected time periods the tail of each rat was transected and template bleeding times were measured. Other endpoints in this study included titration of thrombin activity in plasma (anti-IIa activity) and a determination of whole blood clotting time (HCT). The collected plasma samples from these rats were frozen for subsequent evaluation of the extent of conjugation to plasma proteins using ELISA and western blot analysis.

B. ELISA for the determination of protein bound Argatroban:

Anti-argatroban antibodies from rabbit anti-argatroban polyclonal sera generated in Example 4 was purified by protein A chromatography at a concentration of 3.6 mg/ml and diluted 1/5000 with PBS. Aliquots of 100 µl/well were placed in Nunc Maxisorp 96-well plate and incubated overnight at 4° C. Each well was incubated with 200 µl of PBS-1% BSA at room temperature for 1 hour and subsequently washed 5 times with PBS. Plasma samples collected from the rats at selected time periods were diluted in PBS-1% BSA (dilutions ranging from $1:10^2$ to $1:5\times10^5$ and added at 100 µl well. Argatroban-rat serum albumin conjugates were likewise added at 100 µl/well. The standards were prepared by labeling rat serum albumin (RtSA) with either argatroban derivative (C6-NHS; YS-41-38). The standards were column purified, checked by LC/MS, and the protein concentration of the standards was determined by BCA. All wells were incubated at room temperature for 2 hours and then washed five times in PBS.

The amount of rat albumin-argatroban conjugate bound to the anti-argatroban antibodies was detected by the addition of 100 µl/well of goat anti-RtSA antibodies (Cappel, Cat. #55727), diluted 1:5000 in PBS and preabsorbed with normal rabbit serum (NRbS, Sigma). The plates were incubated at RT for 30 min and washed five times. Biotinylated rabbit anti-Goat IgG (H+L, Vector, Cat. #BA-5000) diluted 1:1000 in PBS-1% BSA, preabsorbed with normal rat serum (NRtS, Sigma), was added at 100 l/well and incubated at room temperature for 30 minutes. Streptavidin-horseradish peroxidase conjugate well (ABC-HRP Vector, PK4000) was then added (100 µl/well, diluted 1:5000 in PBS with 0.1% Tween 20) and incubated at room temperature for 30 minutes. Plates were washed eight times with PBS then twice with distilled water after which 100 µl/well of OPD, 0.5 mg/ml in citrate-phosphate buffer, pH 5.3 with 0.015% $H_2O_2$ was added and incubated at room temperature for 10 minutes, in the dark. Reactions were terminated with the addition of 100 µl/well of 2N sulfuric acid. Optical density, which correlates to the amount of bound RtSA-argatroban conjugates, was determined at 490 nm on SpectraMax 250 plate reader.

Validation studies with this assay method indicate that the method can detect a minimally quantifiable level of 5 ng/ml of RtSA-argatroban in NRtS, with an average background= 0.085 (stdv=0.003). In this method, anti-argatroban antibodies allow for the capture of all argatroban-labeled serum proteins, but only RtSA-argatroban conjugates are detected with the specific anti-RtSA secondary antibodies. Free argatroban can also be captured in this assay and therefore certain levels of free argatroban may inhibit the binding of argatroban-labeled serum proteins.

C. Western-blot analysis:

Plasma samples obtained from the rats were diluted 1:50 in PBS and then further diluted 1:1 with 2× Laemmli non-reducing buffer (Novex). The samples were boiled for 5 min. after which 25 ul of each sample were loaded per well of 8% acrylamide SDS-PAGE precast gel (10 lanes/1 mm gel, Novex). Samples were run in replicates for staining with Coomassie blue and for transfer to nitrocellulose.

Gels were run at a constant voltage of 120 V until the dye fronts reached the bottom of gels. Proteins were transferred to nitrocellulose in 1× Transfer Buffer (Tris-glycine-MeOH) by placing nitrocellulose towards the positive electrode with constant current at 200 mAmps for 3 hours at 4° C. Nitrocellulose blots were placed in 50 ml PBS-1% BSA for 30 minutes. The blots were then placed in a sealed plastic bag containing a solution of 10 ml rabbit anti-argatroban sera generated in Example 4 diluted 1:500 in PBS-1% BSA and incubated overnight at 4° C. The blots were washed three times with 50 ml PBS-1% BSA. Following washing, the blots were incubated in 40 ml of biotinylated goat anti-rabbit IgG (H+L, Vector, BA1000) diluted 1:1000 in PBS-1% BSA and preabsorbed with normal rat serum (NRtS), at room temperature for 30 minutes. The blots were again washed three times with 50 ml PBS-1% BSA, and then incubated in a solution of streptavidin-HRP (Vector, PK4000) diluted 1:500 in PBS-1% BSA at room temperature for 30 minutes. The blots were again washed three times in 50 ml PBS-1% BSA and exposed to 4-chloro-1-naphtol solution (8 ml 4-C-1-N, 3 mg/ml MeOH in 40 ml 10 mM Tris-0.9% NaCl, pH 7.5) for 10 minutes. Blots were placed in distilled water to stop the reaction, air dried and stored in dark to maintain color. Blots were scanned on a HP Scanjet/3c color scanner for storage and reproduction.

The results of the assay indicate that rat albumin, transferrin and IgG bands are labelled by argatroban at both 5 minutes and 24 hours after dosing. In contrast, rats treated with native argatroban alone showed minimal protein association with the anti-argatroban antisera.

EXAMPLE 10

Detection of Argatroban Conjugated to Rabbit Serum Albumin by Direct ELISA

Sera, diluted 1/100 in PBS, were coated on polystyrene microplate wells (NUNC maxisorb) for 1 hour at 37° C., then saturated by PBS containing 5% BSA for 1 hour at 37° C. before washing with PBS containing 0.01% Tween 20 (PBST). Anchored Argatroban was incubated with the biotinylated anti-Argatroban Ab used at 1 µg/ml in PBST for 1 hour at 37° C. Bound antibodies were revealed by incubation for 1 H at 37° C. with alkaline phosphatase conjugated to streptavidin (Bioatlantic; reagent diluted 1/2000 in PBST. Staining was performed with 4 mg pNPP/ml for 30 min at 37° C. Free Argatroban was not detected in this assay, and sensitivity was higher than 3 µM of Arg:RSA 1:1 (RCI product) taken as control.

EXAMPLE 11

Detection of Argatroban by Inhibition Assay

An inhibition assay to quantify levels of free argatroban and protein-bound argatroban was performed using RSA conjugated both to Argatroban and to biotin. Briefly, RSA was conjugated with NHS-Argatroban (ratio 6.6/1), and biotinylated with NHS-biotin (ratio 10/1) and dialyzed against PBS. Microplates (NUNC maxisorb) were coated overnight at 4° C. with rabbit anti-argatroban polyclonal antibodies (IgGAM fraction) at 10 µg/ml in 100 mM carbonate, pH 9.6, washed with PBS, saturated with PBS containing 5% BSA for 1 hour at 37° C., and finally washed with PBS containing 0.05% Tween20 (PBST). Samples of sera treated with argatroban derivatives were diluted in PBST containing 0.5% BSA (PBSTB) and were mixed with the conjugate diluted 1/200,000 in PBSTB (thus 1/400,000 final) and were added to the anti-argatroban coated wells and incubated for 1 hour at 37° C. After PBST washes, bound biotin was revealed by alkaline phosphatase conjugated to Streptavidin diluted 1/20,00 in PBSTB (Bioatlantic). Staining was performed with 4 mg pNPP/ml for 30 min at 37° C. The sensitivity of the assay was 3–15 nM of free Argatroban.

EXAMPLE 12

Determination of Argatroban Concentration in Biological Samples

Anti-argatroban antibodies according to the present invention can be utilized to determine the concentration of free argatroban or argatroban derivatives, or argatroban conjugates in biological samples, including blood samples, of patients being treated for thrombosis. Accurate monitoring of these concentrations will aid a physician in controlling the effective amounts of argatroban in a patient at any given time during treatment. The antibodies can form the basis for immunoassays, including radioimmunoassays, ELISA assays (enzyme-linked immunosorbent assays), immunofluoresence assays, latex agglutination, hemagglutination, chemiluminescence, laser scattering, evanescent light tests, immunohistochemical analysis, tissue labelling tests and the like.

The immunoassays utilizing the anti-argatroban antibodies can further be manufactured into test kits suitable for use in clinical laboratories or by a physician or other health care worker, and will include all the necessary reagents to perform the assay including standards and controls. The test kits can be designed for both qualitative and/or quantitative determination of argatroban or argatroban derivative or conjugate levels.

EXAMPLE 13

Preparation of Monoclonal Antibodies Specific for Argatroban and Argatroban Derivatives An immunogen of the argatroban derivative of Example 1 was conjugated to a KLH carrier protein, similar to the method of Example 2 above. The resultant conjugate was used to immunize mice for the preparation of murine monoclonal antibodies. A group of mice were initially immunized with 50 µg of the KLH-argatroban conjugate emulsified in Freund's complete adjuvant (CFA) per mouse, injected intraperitoneally (IP). A booster injection of 50 µg conjugate emulsified in Incomplete Freund's adjuvant (IFA), injected IP, was given three weeks later and serum samples were taken 5 days later. A selected mouse was given final boost two weeks later, and was sacrificed four days following and its spleen was collected.

Splenocytes were harvested from the spleen, washed and 100×10$^6$ of the splenocytes were fused with murine myeloma cells SP/20-Ag14 according to standard methods known in the art. The remaining splenocytes were frozen at −80° C. for later use. The resulting hybridomas were plated in 96-well tissue culture plates in RPMI media and were selected using HAT media. Approximately 1 week after the fusion, the hybridomas were screened by indirect ELISA, using HSA-argatroban-coated microtiter plates (plated at 5 µg/ml; 50 µl/well), for the secretion of anti-argatroban antibodies. Selected hybridoma colonies were amplified and tested again by ELISA, immunoblotting assays and competition ELISA using free argatroban. Positive colonies were identified and cloned by limiting dilution method and expanded. Clones 7H7 and 9C10 were selected and expanded for monoclonal antibody production. These two hybridoma cell lines have been deposited with the American Type Culture Collection (ATCC) (Manassas, Va.) and been given ATCC Accession Nos. and PTA-3722, respectively.

EXAMPLE 14

Detection of Argatroban Derivative By Immunoblot Ex-vivo Preparation of the Conjugate Twenty µL at 500 µM of the argatroban derivative of Example 1 were added to 1980 µL of citrated Normal Rabbit Plasma. The conjugation of argatroban derivative to plasma proteins was allowed to take place under gentle agitation for 3 h at R.T. The efficiency of the conjugation was checked by Liquid Chromatography/Mass Spectroscopy (LC/MS). Samples were aliquoted and stored at −20° C. until their use.

Western-blot:

Rabbit plasma samples from animals treated with the argatroban derivative were diluted 1/10 in Tris-Buffered Saline (TBS). Ten microliters of diluted samples were mixed with electrophoresis buffer and separated by SDS-PAGE using an 8% polyacrylamide gel, under non-reducing conditions. Plasma proteins were then transferred onto nitrocellulose membrane with a transfer apparatus. Efficacy of bands proteins transfer was checked by reversible staining with 1% Ponceau Red. Nitrocellulose membrane was saturated with TBS containing 3% gelatin or milk and 0.1% Tween 20, for over night at RT to minimize non specific binding. After three washes with TBS-0.1% Tween 20 (TBS-T), the membrane was incubated with anti-Argatroban Monoclonal antibody (Mab) 9C10 from Example 13, labelled to Biotin diluted at 1/2500 in TBS, for 2 h at RT. The membrane was washed three times with TBS-T, and then incubated with Streptavidin-Peroxidase (*Jackson Immuno-Research*) diluted at 1/100,000 in TBS. Development was performed by using ECL method (*Amersham Pharmacia biotech*) with a 1 to 3 min exposure depending on the desired intensity.

The results of the western blotting indicate that the 9C10 Mab-anti Argatroban recognize the argatroban derivative of Example 1 that is bound to rabbit plasma proteins (fibrinogen, IgG, transferrin and Albumin) in both plasma samples and positive control (ex-vivo conjugated argatroban derivative rabbit plasma proteins.

EXAMPLE 15

Sandwich ELISA for the detection of an Argatroban Derivative

Flat-bottomed micro-ELISA plates (Nunc) were coated at 4° C. overnight or at 37° C. for 3 h with 100 µL of goat anti-HSA (Harlan; Sera-lab.) diluted at 1/5000 in 0.05 M sodium carbonate buffer, pH 9.6. Plates were then washed three times with 0.05M phosphate, 0.15 M NaCl buffer, pH 7.4, containing 0.55 g of Tween 20/L (PBS-T), and subsequently blocked with 0.5% gelatin in PBS-T (w/v) for 1 h at 37° C. After three washes, 100 µL/well argatroban derivatized biological plasma protein were added at final concentrations of 50, 100, 500, 1000, 2500, 5000, and 10,000 pM of the argatroban derivative and the plates incubated at 37° C. for 1.5 h. The plates were then washed three times with PBS-T, and 100 µL of the 9C10 monoclonal anti-Arg at 1 µg/mL was added to the wells, and allowed to incubate at 37° C. for 1.5 h. After three more washings, 100 µL of the alkaline phosphatase affinity pure donkey anti-mouse IgG (H+L), (*Jackson Immuno Research*) diluted at 1/10,000 in PBS was added to all wells and plates incubated at 37° C. for 1 h. Revelation of the captured HSA-Argatroban derivative conjugate was performed by adding 100 µL of the substrate solution (1 mg of p-nitrophenyl phosphate disodium salt/ mL, in 0.1 M diethanolamine buffer, pH 9.8) (Sigma). The plates were allowed to develop at 37° C., and absorbance data determined on an ELISA plate reader fitted with a 405 nm filter.

EXAMPLE 16

Immunohistochemistry

Blocks of rabbit carotid tissue treated with different concentrations of the argatroban derivative from Example 1 ranging from 25 µM to 3.125 were sectioned at a thickness of 5 µm on a rotary microtome. Sections were then stretched on a water bath, then collected on microscope slides. The slides were dried overnight at 37° C. The sections were routinely deparaffined in xylene, and rehydrated through a descending alcohol series, then rinsed in deionized water and Phosphate Saline Buffer (PBS). At this point, endogenous peroxidase was blocked by incubating slides with 1% $H_2O_2$ in 50% alcohol for 30 min at RT. Following the blocking step, the sections were rinsed in deionized water and PBS, then incubated with permeabilisation solution (0.1% triton X-100 in 0.1% Na Citrate) for 15 min at RT. Once rinsed, non-specific staining of the slides was reduced by blocking for 60 min with 0.5% gelatin in PBS. Slides were after that incubated with Mab 9C10 anti-Argatroban labeled to Biotin at either 1/50, 1/100, or 1/200 in PBS for 90 min in a humidified chamber at RT. After being rinsed in PBS (3×5 min), slides were treated for 30 min with ExtrAvidin labeled to peroxidase diluted at 1/50 in PBSat RT. Following rinses (3×5 min) with PBS, final color was accomplished by treating slides with 0.5% diaminobenzidine hydrochloride (DAB) and 0.01% $H_2O_2$ in PBS for 10 min. This reaction was terminated by washing the slides in deionized water and 3×5 min PBS. The slides were then dehydrated in ascending alcohols, cleared in xylene, and glass cover slips were mounted with permamount. Negative control slides were prepared by substitution of PBS for Mab 9C10 labeled to Biotin.

EXAMPLE 17

Pharmaceutical Preparations of Anti-argatroban Antisera which Neutralize the Thrombolytic Activity of Argatroban The administration of argatroban derivatives to patients that covalently bond to serum proteins and cellular blood components leads to a concern over the side effects associated with thrombosis treatment using derivatized argatroban, including hemorrhaging. The antibodies of the present invention can be utilized to inactivate, sequester and remove, either directly or indirectly, the argatroban derivatives and resulting conjugates from a patient's bloodstream.

A. Ex vivo immunoadsorbtion

Anti-argatroban antibodies can be used to remove argatroban or argatroban derivatives and conjugates from a patient's blood ex vivo by contacting the blood with the antibodies under sterile conditions. For example, the antibodies can be fixed or otherwise immobilized on a column matrix and the patient's blood, via catheter or other means can be removed from the patient and passed over the matrix. Argatroban or its derivatives or conjugates will bind to the antibodies and the blood containing lower concentration of argatroban or its derivatives or conjugates will be returned to the patient's circulatory system. By adjusting pressure and flow rate, the amount of argatroban, argatroban derivatives and/or conjugates can be controlled. In like methods, the preferential removal of argatroban and its derivatives and conjugates from the serum component of a patient's blood can be effected, for example, by the use of a semipermeable membrane, or by otherwise first separating the serum component from the cellular component, by ways known in the art, prior to passing the serum component over an anti-argatroban matrix. Alternatively, the preferential removal of argatroban-conjugated blood cells, including red blood cells, can also be effected by collecting and concentrating the blood cells of the patient's blood and contacting these cells with fixed anti-argatroban antibodies to the exclusion of the serum component of the patient's blood.

B. Parenteral administration (passive immunization)

Anti-argatroban antibodies can be administered to a patient that has received argatroban derivatives for thrombosis treatment. The antibodies will bind the derivatives and resulting conjugates. Once bound, the activity of the argatroban will be hindered if not completely blocked, thereby reducing the biologically effective concentration of argatroban in the patient's blood stream and minimizing harmful side effects. In addition, the bound antibody-argatroban complex will facilitate the clearance of the argatroban derivatives and conjugates from a patient's bloodstream, thereby reducing the actual concentration of argatroban in the patient's blood.

EXAMPLE 18

Preparation of MAbs Specific for Diastereoisomers of Argatroban

Argatroban is commercially available as a mixture of two diastereoisomers at position 21 (R and S isomers) with a ratio 65%–35% R and S isomers, respectively. Recently, there have been changes in how diastereomeric and enantiomeric mixtures are accepted by the public and by all regulatory institutions. Moreover, studies performed on each isomer of argatroban by T. Rawson et al, J. Pharm. Sciences, 1993, 82, 672–673, incorporated herein by reference, has shown that both isomers of argatroban have a different PK and reactivity profile in bleeding assay. It is expected that purified R and S forms of argatroban may have different and preferred activities. Current methods of separating isomers of argatroban are costly and cumbersome, e.g., HPLC non-chiral separation, performed on very small scale. Therefore, there is a need to easily identify and separate argatroban isomers on a large scale.

To meet this need, we prepared an immunogen of a modified argatroban conjugated to a KLH carrier protein, similar to the method of Example 2 above. Specifically, the argatroban used to prepare the immunogen was a mixture of R and S isomers at a 65:35 ratio of R to S. The argatroban was modified at its piperidine moiety, away from the chiral center at position 21.

The resultant conjugate was used to immunize mice for the preparation of monoclonal antibodies according to conventional methods. The mice (98015 and 98016) were initially immunized with 50 µg of the KLH-argatroban conjugate emulsified in Freund's complete adjuvant (CFA) per mouse, injected intraperitoneally (IP). A booster injection of 50 µg conjugate emulsified in Incomplete Freund's adjuvant (IFA), injected IP, was given three weeks later and serum samples were taken 5 days later. Mouse 96015 was selected and given final boost two weeks later, and was sacrificed four days following and its spleen was collected.

$200 \times 10^6$ splenocytes were harvested from the spleen, washed and $100 \times 10^6$ of the splenocytes were fused with murine myeloma cells SP/20-Ag14 according to standard methods known in the art. The remaining splenocytes were frozen at −80° C. for later use. The resulting hybridomas were plated in 96-well tissue culture plates in RPMI media and were selected using HAT media. Approximately 1 week after the fusion, the hybridomas were screened by indirect ELISA, using HSA-argatroban-coated microtiter plates (HSA-argatroban conjugate including both R and S isomers, plated at 5µg/ml; 50 µl/well), for the secretion of anti-argatroban antibodies. Selected hybridoma colonies were amplified and tested again by ELISA, immunoblotting assays and competition ELISA using free argatroban. Positive colonies were identified and cloned by limiting dilution method, expanded, and Ig class was determined. The clones were then separately screened by ELISA against R isomers of argatroban and 3 isomers of argatroban. Clones which were specific for one isomer and which did not appreciably cross-react with the other isomer were then selected, and expanded for monoclonal antibody production.

Without being bound to theory, we believe that only a few epitopes are available on a small molecule such as argatroban for antibody recognition. The smaller the molecule, the deeper in the α-loops of the Fv the molecule has to penetrate to bind to the antibody. The diastereoisomers of argatroban are at position 21 on the tetrahydroquinoline ring, at the opposite side of the modified piperdine ring of the molecule. We believe that the tetrahydroquinoline ring binds deep in the binding pocket of a reactive antibody, leading to different populations of antibody clones, including stereospecific clones.

EXAMPLE 19

Affinity Chromatography Separation of Diastereoisomers of Argatroban and of derivatives of argatroban Monoclonal antibodies generated as described in Example 16 can be used for affinity purification of diastereoisomers of argatroban as well as for the affinity purification of diastereoisomers of derivatives of argatroban. Identified hybridoma clones have been scaled up in ascites fluid and the secreted monoclonal antibodies have been purified using Protein A chromatography. The purified MAbs will be used to prepare R-specific and S-specific affinity matrices. Solutions of argatroban or derivatives containing R and S isomers can be loaded on either matrix and the specific isomers allowed to bind to the column while unbound isomers will pass through the column. The bound isomers can then be eluted by varying the conditions, e.g. by varying pH or salt concentrations. The purification scheme is shown in the scheme below using a derivative of argatroban precursor of argatroban C6-NHS.

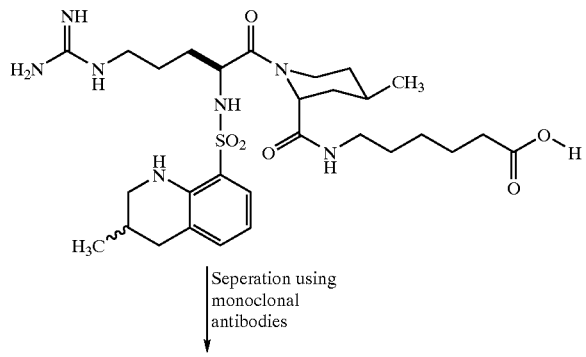

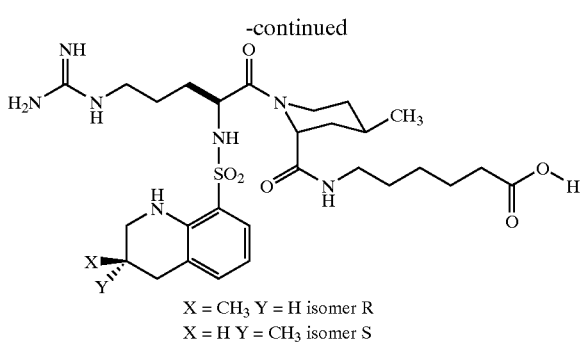

X = CH₃ Y = H isomer R
X = H Y = CH₃ isomer S

The invention now being fully described, it will be apparent to one of ordinary skill in the art that many changes, variations, and modifications can be made thereto without departing from the spirit and scope of the invention or any embodiment thereof.

We claim:

1. An isolated monoclonal antibody that specifically binds argatroban and argatroban derivatives, wherein said monoclonal antibody is produced by hybridoma cell line 9C10 having A.T.C.C. Accession No. PTA-3772, wherein said argatroban derivatives are selected from the group consisting of argatroban-C6-NHS, argatroban-C12-NHS, argatroban-C13-maleimide, argatroban-C21-PE-maleimide, and argatroban-C18-maleimide.

2. The antibody of claim 1, wherein said antibody specifically binds argatroban-C6-NHS.

3. The antibody of claim 1, wherein said monoclonal antibody specifically binds S-argatroban.

4. The antibody of claim 1, wherein said monoclonal antibody specifically binds R-argatroban.

5. A kit for detecting the concentration of argatroban or argatroban derivatives in a biological sample comprising the antibody of claim 1.

6. The kit of claim 5, wherein said biological sample is a blood sample.

7. The kit of claim 5 further comprising reagents for performing immunoassays selected from the group consisting of ELISA, RIA, Western Blot, immunohistochemistry and flow cytometry reagents.

8. The kit of claim 7 further comprising a second antibody or fragment thereof that specifically binds to the monoclonal antibody produced by hybridoma cell line 9C10 having A.T.C.C. Accession No. PTA-3772, wherein said second antibody or fragment thereof is conjugated to an indicator reagent, said indicator reagent including a signal generating compound capable of generating a measurable signal.

9. The antibody of claim 1, wherein said antibody specifically binds to an argatroban derivative conjugated to a blood component.

10. The antibody of claim 9, wherein said antibody specifically binds to an argatroban derivative conjugated to a serum protein.

* * * * *